United States Patent
Isaka et al.

(10) Patent No.: US 10,054,573 B2
(45) Date of Patent: Aug. 21, 2018

(54) METHOD FOR FITTING PROTECTION TUBE TO GAS SENSOR

(71) Applicant: NGK INSULATORS, LTD., Nagoya-shi, Aichi (JP)

(72) Inventors: Kenji Isaka, Nagoya (JP); Nobukazu Ikoma, Nagoya (JP); Yutaka Nakane, Okazaki (JP)

(73) Assignee: NGK INSULATORS, LTD., Nagoya (JP)

( * ) Notice: Subject to any disclaimer, the term of this patent is extended or adjusted under 35 U.S.C. 154(b) by 554 days.

(21) Appl. No.: 14/642,212

(22) Filed: Mar. 9, 2015

(65) Prior Publication Data

US 2015/0260697 A1 Sep. 17, 2015

(30) Foreign Application Priority Data

Mar. 12, 2014 (JP) .................. 2014-048581

(51) Int. Cl.
*G01N 27/407* (2006.01)
*G01N 33/00* (2006.01)
*H01R 43/00* (2006.01)

(52) U.S. Cl.
CPC ..... *G01N 33/0009* (2013.01); *G01N 27/4077* (2013.01); *H01R 43/005* (2013.01); *Y10T 29/49826* (2015.01); *Y10T 29/53961* (2015.01)

(58) Field of Classification Search
CPC ............ G01N 33/0009; G01N 27/4077; Y10T 29/49826; Y10T 29/53961; H01R 43/005
See application file for complete search history.

(56) References Cited

U.S. PATENT DOCUMENTS

| 6,342,140 B1 | 1/2002 | Weyl et al. |
| 2001/0054552 A1* | 12/2001 | Matsuo ................ G01N 27/407 204/421 |
| 2014/0102170 A1 | 4/2014 | Kato |

FOREIGN PATENT DOCUMENTS

| JP | 4194660 B2 | 10/2008 |
| WO | 2013/005491 A1 | 1/2013 |

* cited by examiner

*Primary Examiner* — Sarang Afzali
*Assistant Examiner* — Ruth G Hidalgo-Hernande
(74) *Attorney, Agent, or Firm* — Global IP Counselors, LLP (57) ABSTRACT

A method for fitting a protection tube to a gas sensor includes: a step for engaging tube-end opening jigs which have been inserted into the inside of a protection tube through its one end portion, with this end portion, for maintaining this end portion at an opened state, a step for bringing tube-end holding jigs into contact with this engagement portion from outside for holding the tube through pinching between these jigs, and a step for inserting the sensor into the inside of the tube being held through pinching, wherein the insertion of the sensor into the inside of the tube is continued even after an end portion of the sensor comes into contact with the inner surface of the tube, while the engagement of the tube with the tube-end opening jigs is gradually released, thereby fitting the tube to the sensor.

7 Claims, 10 Drawing Sheets

METHOD FOR FITTING PROTECTION TUBE TO GAS SENSOR

BACKGROUND OF THE INVENTION

Field of the Invention

The present invention relates to processing for fitting a tube for protecting cables to a gas sensor.

Description of the Background Art

Conventionally, there have been well known gas sensors having sensor elements formed from an oxygen-ion conductive solid electrolyte ceramic, such as zirconia ($ZrO_2$), as devices for determining the concentrations of predetermined gas components in measurement gas, such as combustion gasses and exhaust gasses in internal combustion engines such as automobile engines.

Generally, such a gas sensor interiorly includes a sensor element (detection element) with an elongated plate shape which is made of a ceramic and, also, is structured to be covered, over its outer side, with a member called a cover or a casing. From this cover or the like, cables (connection conductors) for electrically connecting the sensor element to an external drive controller are properly extended outward (refer to International Publication WO 2013/005491 and Japanese Patent No. 4194660).

Such a gas sensor is used in an environment under an atmosphere containing gasses being at higher temperatures and having reactivity and corrosivity or in an environment therearound, such as exhaust ports of internal combustion engines. Therefore, it is necessary to cover the cables with a protection tube having incombustibility, corrosion resistance and the like, in order to prevent the cables from being deformed, deteriorated and corroded due to such an environment. In this case, the protection tube is required to be certainly fitted and secured to the gas sensor.

For example, if a protection tube for covering cables is provided in a gas sensor disclosed in International Publication WO 2013/005491, the protection tube is required to be fitted to an end portion of the gas sensor. Generally, the gas sensor is thicker than the bundle of the cables or both of them have substantially the same thickness and, therefore, it is necessary to expand the tip end portion of the protection tube, in attaining this fitting. In order to prevent the cables from being exposed, it is necessary to prevent the occurrence of cracks and breakages at the tip end portion of the protection tube, in performing this fitting. Further, in order to prevent disengagement of the protection tube, the fitting and securing thereof to the gas sensor should be certainly attained at a predetermined position.

Japanese Patent No. 4194660 discloses a formed hose provided at its end portion with a securing portion to be fitted to a casing of a gas sensor and with a transition portion extending in a conical shape, in an aspect for preventing intrusion of contaminations therein. However, the provision of the securing portion and the conical portion in the formed hose causes an increase of the fabrication cost for the gas sensor.

SUMMARY OF THE INVENTION

The present invention relates to a method for fitting a tube for protecting cables to a gas sensor, and an apparatus for realizing the same.

According to the present invention, there is provided a method for fitting a tube for protecting cables to a gas sensor, wherein the method includes the steps of: a) maintaining one end portion of the protection tube at an opened state with a tube-end opening jig, the tube-end opening jig being configured to be inserted into inside of the protection tube through the one end portion of the protection tube to engage the one end portion of the protection tube with the tube-end opening jig; b) holding the protection tube through pinching between a tube-end holding jig and the tube-end opening jig, the tube-end holding jig being configured to come into contact with the protection tube at its portion which is engaged with the tube-end opening jig, from outside of the protection tube; and c) inserting the gas sensor into inside of the protection tube being held through pinching by the tube-end holding jig and the tube-end opening jig, the insertion of the gas sensor into the inside of the protection tube being configured to be continued even after an end portion of the gas sensor comes into contact with an inner surface of the protection tube, while the engagement of the protection tube with the tube-end opening jig is gradually released, thereby fitting the protection tube to the gas sensor.

This enables fitting the protection tube to the gas sensor without inducing displacements of the protection tube.

Preferably, the tube-end opening jig is constituted by a pair of tube-end opening jigs, and each of the pair of the tube-end opening jigs has a tapered portion such that a distance to the companion tapered portion paired therewith gradually decreases with decreasing distance to its end portion, and in the step a), the tapered portions are inserted into the inside of the protection tube.

This enables easily and certainly engaging the protection tube with the pair of the tube-end opening jigs, without inducing cracks and breakages at its end portion.

Further, in another aspect of the present invention, there is provided an apparatus for fitting a protection tube to a gas sensor, wherein the protection tube fitting apparatus is an apparatus for fitting a protection tube for protecting cables to a gas sensor, and the protection tube fitting apparatus includes: fixing element for placing and fixing a gas sensor thereon and thereto, the fixing element being movable in a horizontal direction; a tube-end opening jig configured to be inserted into inside of the protection tube from its one end portion to be engaged with the one end portion of the protection tube for maintaining the one end portion of the protection tube at an opened state; and a tube-end holding jig configured to come into contact with the protection tube from outside of the protection tube, at its portion which is engaged with the tube-end opening jig, for holding the protection tube through pinching between the tube-end holding jig and the tube-end opening jig; wherein the tube-end opening jig is configured to engage with the one end portion of the protection tube for maintaining the one end portion of the protection tube at the opened state, the tube-end holding jig and the tube-end opening jig are enabled to secure the protection tube through pinching, the gas sensor is inserted into the inside of the protection tube by moving the fixing element securing the gas sensor thereto, with the protection tube being secured through pinching by the tube-end holding jig and the tube-end opening jig, and after an end portion of the gas sensor inserted into the inside of the protection tube comes into contact with an inner surface of the protection tube, the insertion of the gas sensor into the inside of the protection tube is continued, while the engagement of the protection tube with the tube-end opening jig is gradually released, thereby fitting the protection tube to the gas sensor.

This enables fitting the protection tube to the gas sensor without inducing displacements of the protection tube.

Preferably, the tube-end opening jig is constituted by a pair of tube-end opening jigs, each of the pair of the tube-end opening jigs has a tapered portion such that a distance to the companion tapered portion paired therewith gradually decreases with decreasing distance to its end portion, and the one end portion of the protection tube is brought into the opened state by inserting the tapered portions into the inside of the protection tube for bringing.

This enables easily and certainly engaging the protection tube with the pair of the tube-end opening jigs, without inducing cracks and breakages at its end portion.

Accordingly, it is an object of the present invention to provide a method which enables preferably fitting, to a gas sensor, a protection tube for protecting cables necessary therefor.

These and other objects, features, aspects and advantages of the present invention will become more apparent from the following detailed description of the present invention when taken in conjunction with the accompanying drawings.

DESCRIPTION OF THE PREFERRED EMBODIMENTS (The External Appearance and the Structure of Gas Sensor)

Figure 1:
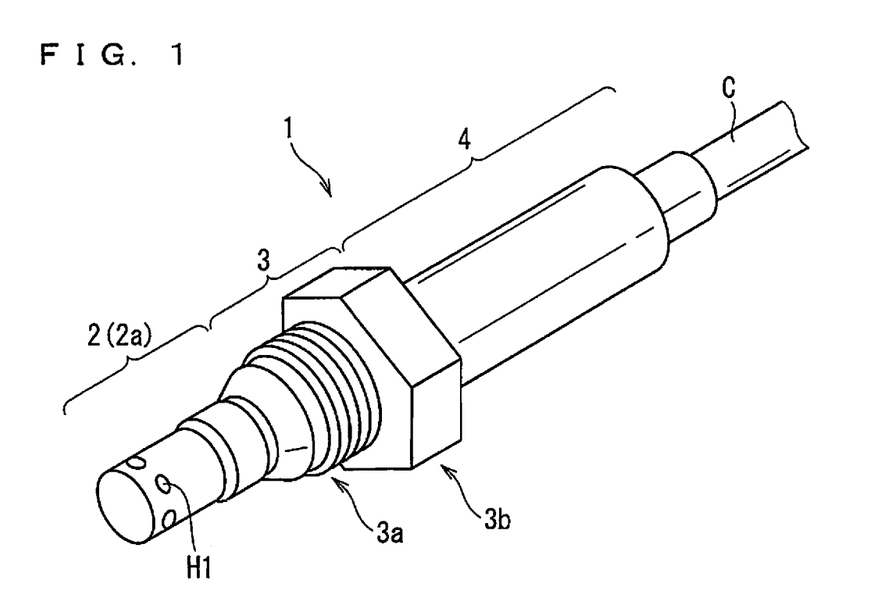
FIG. 1 is a perspective view of an external appearance of a gas sensor 1.

FIG. 1 is a perspective view of an external appearance of a gas sensor (more specifically, the main body thereof) 1 which is to be subjected to fitting processing which will be described later (before the fitting processing). In the present preferred embodiment, the gas sensor 1 is for detecting a predetermined gas component (for example, NOx and the like), through a sensor element included therein, which is not illustrated.

The outer side portion of the gas sensor 1 is mainly constituted by a first cover 2, a fixing bolt 3, and a second cover 4.

The first cover 2 is an exterior member with an approximately-cylindrical shape which is made of a metal for protecting the portion of the sensor element which directly comes into contact with the measurement gas during usage.

More specifically, the first cover 2 has a double-layer structure of an outside cover 2a and an inside cover (not shown). Each of the outside cover 2a and inside cover has a circular bottom on one side and has a plurality of through holes through which a gas passes in the side portion. FIG. 1 illustrates through holes H1 provided in the outside cover 2a, which are merely an example. The position and number of through holes arranged may be appropriately determined in consideration of how a measurement gas flows into the first cover 2.

The fixing bolt 3 is an annular member made of metal to be used when the gas sensor 1 is fixed at a measurement position. The fixing bolt 3 includes a threaded bolt portion 3a and a held portion 3b to be held when the bolt portion 3a is screwed. The bolt portion 3a is screwed with a nut provided at a position at which the gas sensor 1 is mounted. For example, the bolt portion 3a is screwed with a nut portion provided in the car exhaust pipe, whereby the gas sensor 1 is fixed to the exhaust pipe such that the first cover 2 side thereof is exposed in the exhaust pipe.

The second cover 4 is a cylindrical member made of metal that protects other portion of the gas sensor 1. A cable C for electrically connecting the gas sensor 1 and a drive controller (not shown) extends from the end of the second cover 4. Although, in FIG. 1 and the drawings thereafter, for ease of illustration, the cable C is illustrated as if it is only a single cable, the cable C is formed to be a bundle of plural cables, in actual.

(Protection Tube Fitting Apparatus and Fitting Processing Using the Same)

Next, there will be described protection tube fitting processing which is performed according to the present preferred embodiment. The protection tube fitting processing according to the present preferred embodiment is processing for fitting and securing a protection tube 5 (see FIGS. 3A and 3B) for covering and protecting the cable C, to the gas sensor 1. The protection tube 5 is a tube having incombustibility or corrosion resistance and also having flexibility, such as a varnished tube, for example.

Briefly, in the present preferred embodiment, the gas sensor 1 is prepared, wherein the gas sensor 1 has been formed by annularly mounting the protection tube 5 to the portion of the cable C, beforehand, in a preparation process. Further, the protection tube 5 is opened at its end portion, and, an end portion of the second cover 4 is covered with this opened portion of the protection tube 5 to fit the protection tube 5 to the gas sensor 1. Thereafter, processing for securing the fitting portion by an ear clamp 6 (see FIGS. 3A and 3B) is performed.

Figure 2:
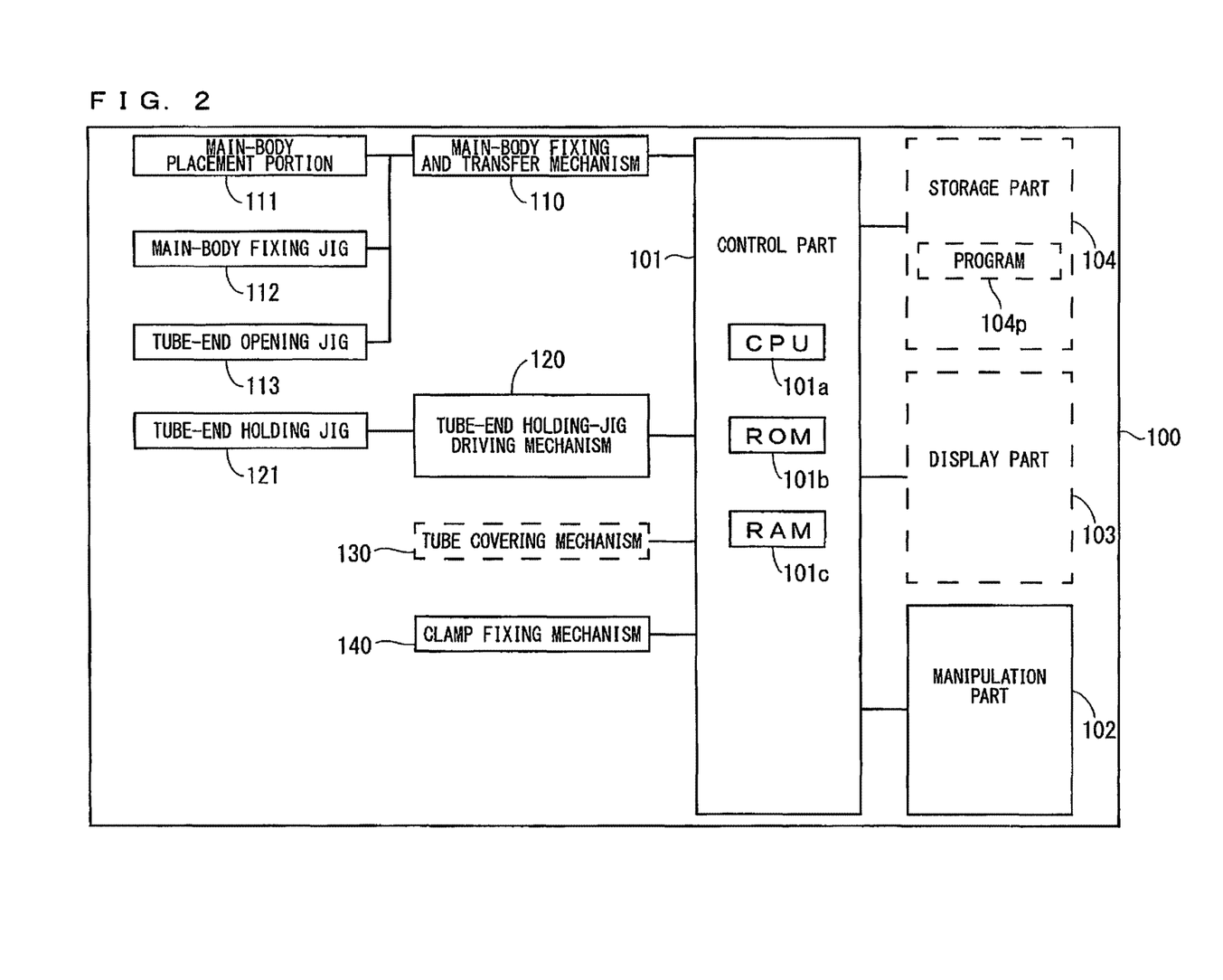
FIG. 2 is a block diagram schematically illustrating the structure of a fitting apparatus 100.

FIG. 2 is a block diagram schematically illustrating the structure of the fitting apparatus 100 for use in this fitting processing.

The fitting apparatus 100 includes a control part 101 for controlling the overall operations of the fitting apparatus 100, wherein the control part 101 is constituted by a CPU 101a, a ROM 101b, a RAM 101c and the like. The fitting apparatus 100 further includes a manipulation part 102 forming an input interface which is constituted by switches, buttons, a touch panel and the like for generating various types of execution commands to the fitting apparatus 100. Moreover, the fitting apparatus 100 may include a display part 103 constituted by a display and measuring instruments for displaying various types of operation menus and operation states of the fitting apparatus 100, and may include a storage part 104 which stores operation condition data and the like which are not illustrated. For example, the storage part 104 stores an operation program 104p for the fitting apparatus 100, and this operation program 104p is executed by the control part 101, so that a series of fitting processing operations which will be described later are automatically performed.

The fitting apparatus 100 further includes a main-body fixing and transfer mechanism 110, a main-body placement portion 111, a pair of main-body fixing jigs 112, a pair of tube-end opening jigs 113, a tube-end holding-jig driving mechanism 120, a pair of tube-end holding jigs 121, and a clamp securing mechanism 140, as components for performing actual fitting operations. Further, the fitting apparatus 100 may also include a tube covering mechanism 130.

The main-body placement portion 111 is a portion for placing the gas sensor 1 thereon during the fitting processing. Further, the pair of the main-body fixing jigs 112 are jigs which are provided in this main-body placement portion 111. By activating the main-body fixing and transfer mechanism 110, the pair of the main-body fixing jigs 112 are caused to pinch the gas sensor 1 placed on the main-body placement portion 111, so that the gas sensor 1 is fixed to the main-body placement portion 111.

Further, the main-body fixing and transfer mechanism 110 also performs operations for moving the main-body placement portion 111 in the horizontal direction. Further, these operations for moving the main-body placement portion 111 are realized by a ball screw mechanism, for example.

The pair of the tube-end opening jigs 113 are jigs provided for maintaining one end portion of the protection tube 5 at an opened state, when the protection tube 5 is mounted to the gas sensor 1. This pair of the tube-end opening jigs 113 are adapted to change their positions, in conjunction with the horizontal movement of the main-body placement portion 111 by the main-body fixing and transfer mechanism 110.

The pair of the tube-end holding jigs 121 are a pair of jigs provided for holding the protection tube 5, in order to prevent the protection tube 5 from being displaced, when the gas sensor 1 is inserted into the protection tube 5 being maintained at an opened state at its one end portion by the pair of the tube-end opening jigs 113. The pair of the tube-end holding jigs 121 are caused to perform these holding operations and releasing thereof, through the tube-end holding-jig driving mechanism 120.

The tube covering mechanism 130 is a portion which performs an operation for automatic movement and the like of the protection tube 5, when the protection tube 5 is covered at its end portion being maintained at the opened state with the end portion of the second cover 4.

The clamp securing mechanism 140 is a portion adapted to perform processing for securing (fastening) the portion to which the protection tube 5 has been fitted, by the ear clamp 6 which is an annular fastening member.

FIGS. 3 to 10 are schematic plan views illustrating states halfway through fitting processing, in a case where the fitting processing for fitting the protection tube 5 to the gas sensor 1 is performed using the fitting apparatus 100. In this case, in the respective drawings in FIGS. 3 to 10, it is assumed that the main-body placement portion 111 is freely moved in the leftward and rightward directions when viewed in the drawings, due to effects of the main-body fixing and transfer mechanism 110.

Figure 3A:
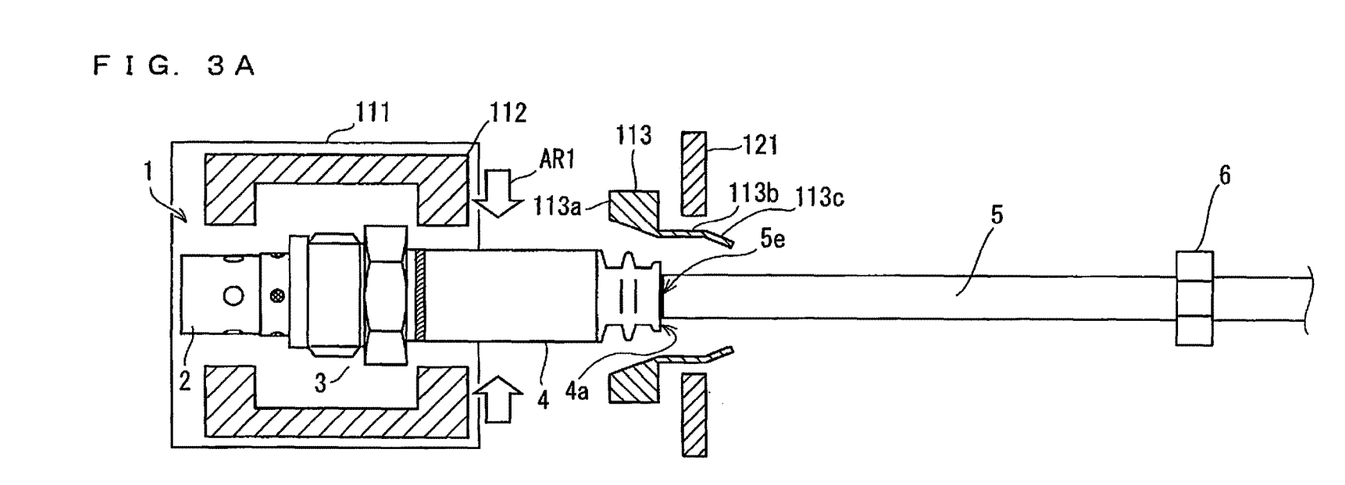
FIGS. 3A and 3B, 4A and 4B, 5A and 5B, 6A and 6B, 7A and 7B, 8A and 8B, 9 and 10 are schematic plan views each illustrating a state halfway through fitting processing.

As illustrated in FIG. 3A, in the fitting apparatus 100, the pair of the main-body fixing jigs 112 are placed in such a way as to be spaced apart from each other on the main-body placement portion 111 and, further, the pair of the tube-end opening jigs 113 are provided at positions beside the main-body placement portion 111 within a horizontal plane. The pair of the tube-end opening jigs 113 are provided in such a way as to be spaced apart from each other in the same direction as the direction in which the pair of the main-body fixing jigs 112 are spaced apart from each other.

The pair of the tube-end opening jigs 113 each include a base portion 113a, an arm portion 113b protruding and extending from the base portion 113a, and a tapered portion 113c which is continuous with the arm portion 113b and has a tip end portion with a triangular shape with rounded corners such that the distance to the companion tapered portion paired therewith decreases with decreasing distance to its tip end portion, as illustrated in FIG. 3A. Further, the pair of the tube-end opening jigs 113 are adapted to change the interval therebetween, in conjunction with the horizontal movement of the main-body placement portion 111. More specifically, the pair of the tube-end opening jigs 113 are configured to get farther away from each other if the main-body placement portion 111 gets closer thereto and to get closer to each other if the main-body placement portion 111 gets father away therefrom.

Moreover, as illustrated in FIG. 3A again, in the fitting apparatus 100, the pair of the tube-end holding jigs 121 are provided in such a way as to sandwich, therebetween, the arm portions 113b in the pair of the tube-end opening jigs 113.

In addition, in the fitting apparatus 100, on an extended line in the direction of the movement of the main-body placement portion 111, there is held the ear clamp 6 which has not been fastened (which has not been reduced in diameter) by the clamp securing mechanism 140, which is not illustrated in FIG. 3A.

In order to perform fitting processing, at first, the gas sensor 1 is prepared, wherein the gas sensor 1 has been formed by annularly mounting the protection tube 5 to the portion of the cable C6, beforehand, in a preceding process. Further, the gas sensor 1 is placed on the main-body placement portion 111, in a state where the gable C and the protection tube 5 are passed through the ear clamp 6 which has a larger diameter than the outer diameter of the second cover 4 in the gas sensor 1 and has not been reduced in diameter, as illustrated in FIG. 3A. Further, in FIG. 3A, one end portion 5e of the protection tube 5 is in contact with the end portion 4a of the second cover 4 of the gas sensor 1, but this is not an essential aspect. At this point, the second cover 4 and the protection tube 5 have not yet been coupled to each other and, therefore, the cable C is allowed to expose between both of them.

More specifically, the gas sensor 1 is placed horizontally in such a way as to be positioned between the pair of the main-body fixing jigs 112, such that the second cover 4 is directed toward the pair of the tube-end opening jigs 113. At this time, a portion of the second cover 4 near the end portion 4a (and, further, the cable C to which the protection tube 5 has been annularly mounted) is positioned between the pair of the tube-end opening jigs 113. This is realized because the positions where the pair of the tube-end opening jigs 113 are placed in the fitting apparatus 100 have been preliminarily determined in such a way as to satisfy the aforementioned positional relationship.

Figure 3B:
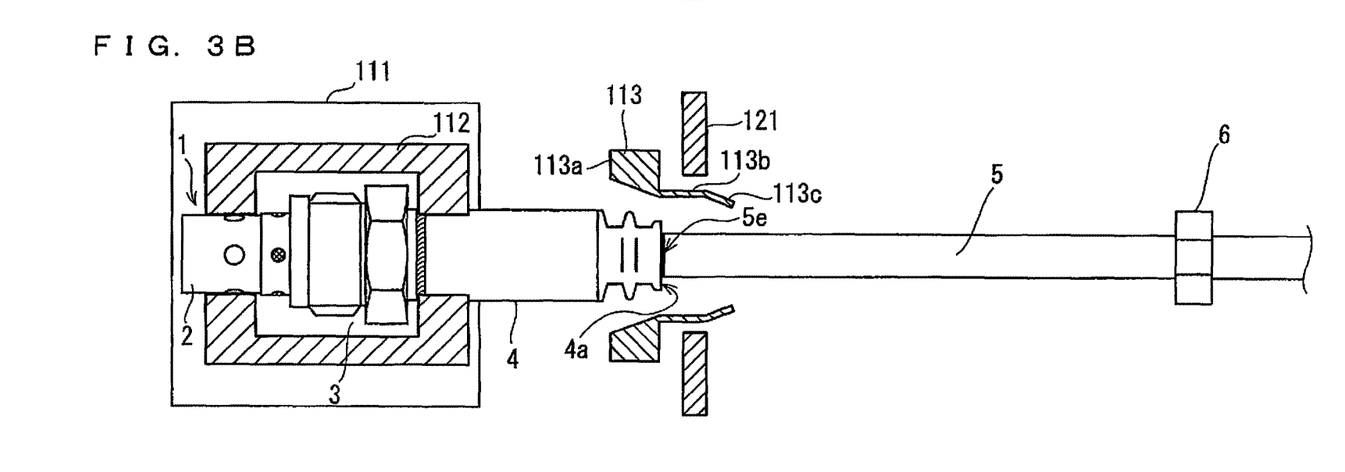

When the gas sensor 1 has been placed on the main-body placement portion 111, the main-body fixing and transfer mechanism 110 is activated, so that the pair of the main-body fixing jigs 112 get closer to the outer side surface of the gas sensor 1 as indicated by arrows AR1 in FIG. 3A and, finally, get to pinch the gas sensor 1 therebetween as illustrated in FIG. 3B. This means that the gas sensor 1 has been fixed to the main-body placement portion 111. This fixing operation by pinching can be appropriately realized through various types of well-known mechanisms, such as ball screw mechanisms.

Figure 4A:
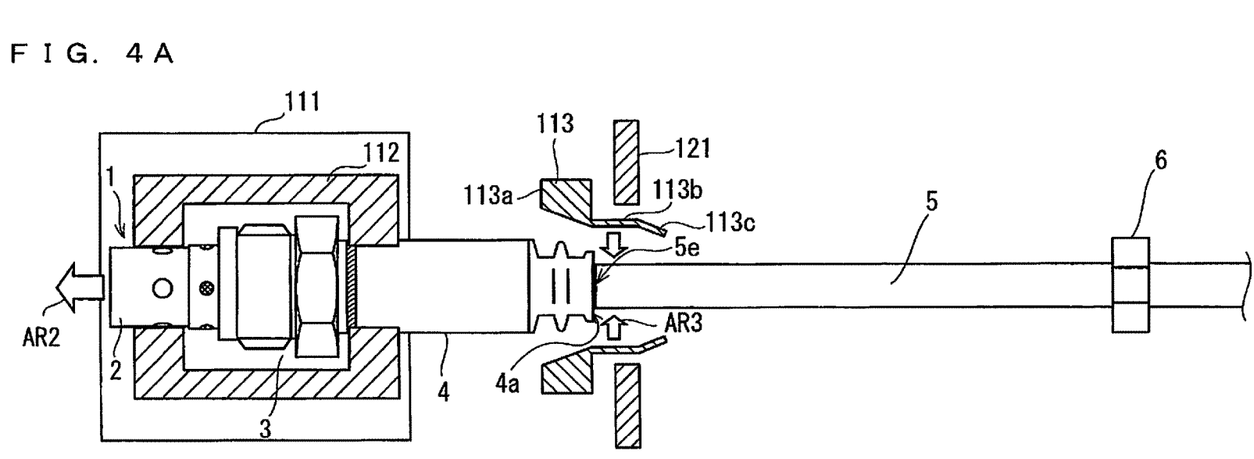
Figure 4B:
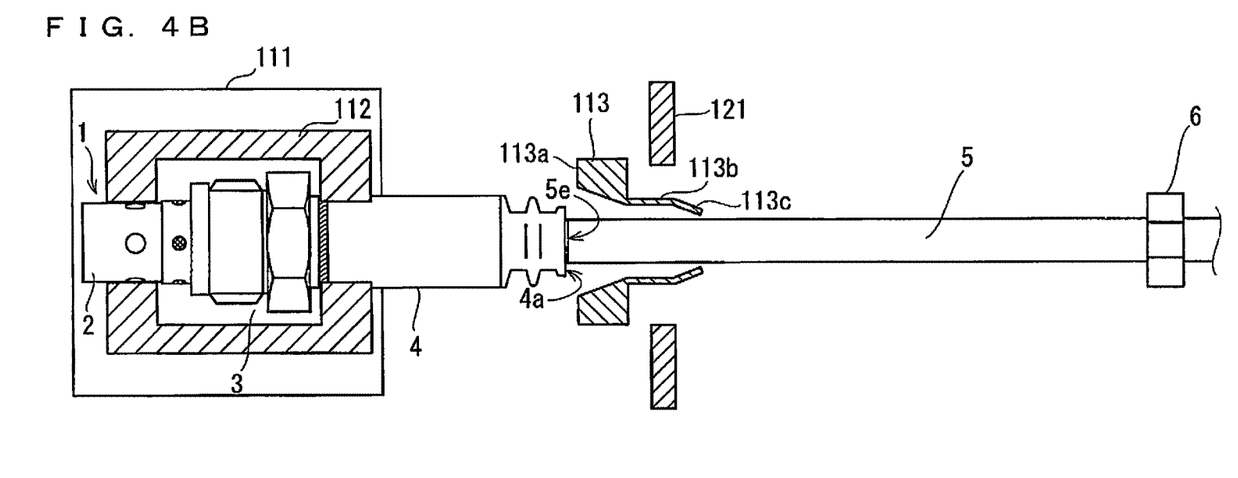

When the gas sensor 1 has been fixed to the main-body placement portion 111 by the pair of the main-body fixing jigs 112, subsequently, the main-body fixing and transfer mechanism 110 is activated, so that the main-body placement portion 111 is moved in the direction in which it gets father away from the pair of the tube-end opening jigs 113, as indicated by an arrow AR2 in FIG. 4A, and, also, in conjunction with this moving operation, the pair of the tube-end opening jigs 113 are caused to get closer to each other, as indicated by arrows AR3 in FIG. 4A. FIG. 4B illustrates a state halfway through getting them closer to each other.

Figure 5A:
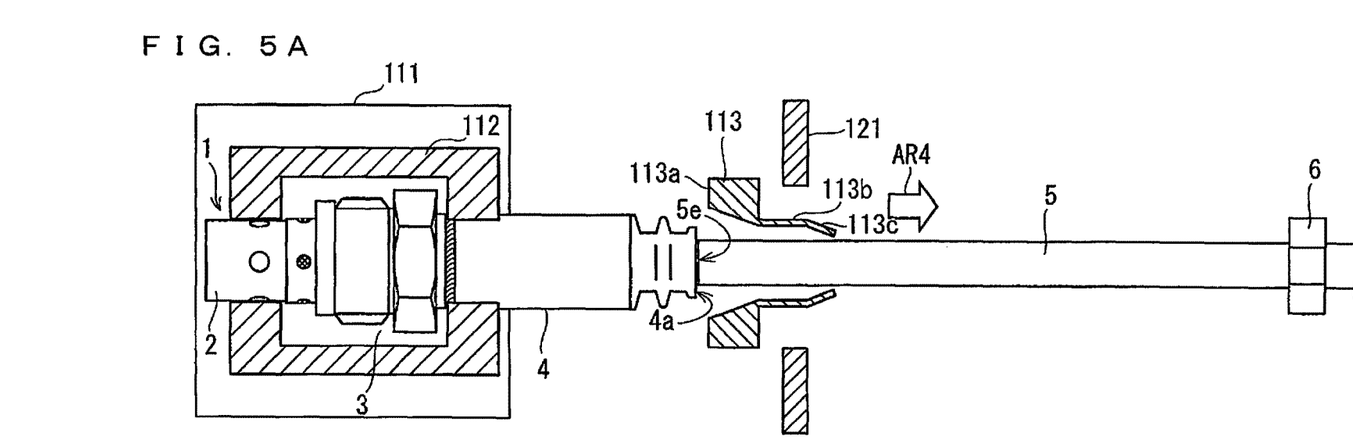
Figure 5B:
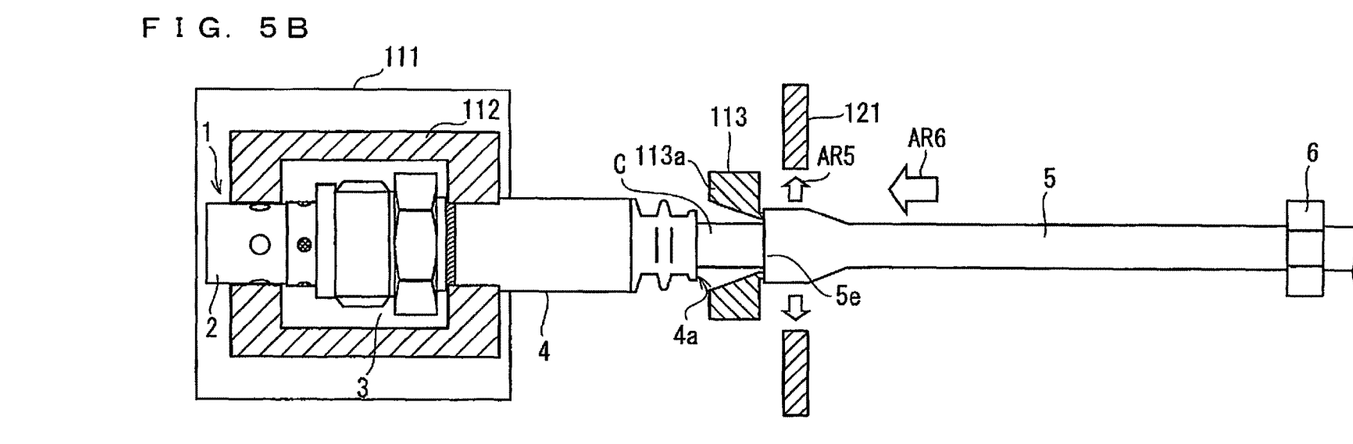

Further, while the interval between the pair of the tube-end opening jigs 113 is reduced, the protection tube 5 is temporarily moved in the direction in which it gets farther away from the pair of the tube-end opening jigs 113, as indicated by an arrow AR4 in FIG. 5A. At the time when the interval between the tip ends of the two tapered portions 113c has gotten substantially equal to the inner diameter of the protection tube 5, the one end portion 5e is slightly widened as indicated by arrows AR5 in FIG. 5B, with the protection tube 5 being gotten closer to the gas sensor 1, again, as indicated by an arrow AR6. Then, there is realized a state where the two tapered portions 113c are inserted into the protection tube 5, so that the one end portion 5e of the protection tube 5 having flexibility is gradually expanded along the shape of the tapered portions 113c and, also, the protection tube 5 is gradually engaged with the two tapered portions 113c and, further, with the two arm portions 113b. Since the two arm portions 113b are spaced apart from each other more largely than the two tapered portions 113c, it is possible to realize engagement of the protection tube 5 with the pair of the tube-end opening jigs 113 in the state where the one end portion 5e is opened. In a case where the arm portions 113b are protruded normally with respect to the surfaces of the base portions 113a, as in the present preferred embodiment, the base portions 113a can function as a stopper for defining the depth of the engagement of the protection tube 5 therewith.

In the fitting apparatus 100, since the pair of the tube-end opening jigs 113 are provided with the tapered portions 113c, it is possible to easily and certainly engage the protection tube 5 with the pair of the tube-end opening jigs 113 even manually, without inducing cracks and breakages in the one end portion 5e.

Figure 6A:
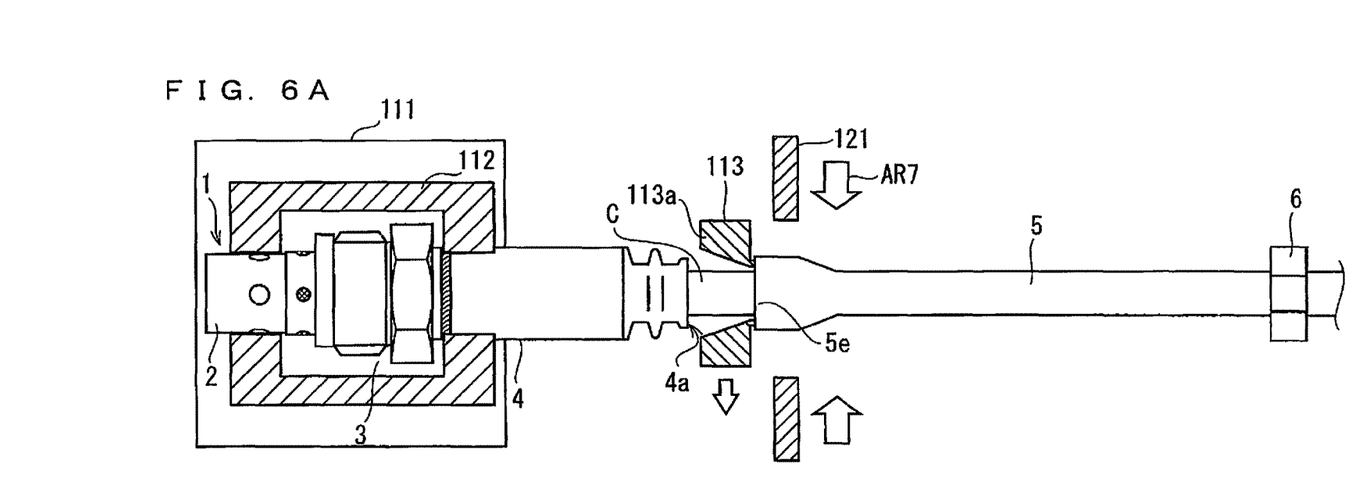
Figure 6B:
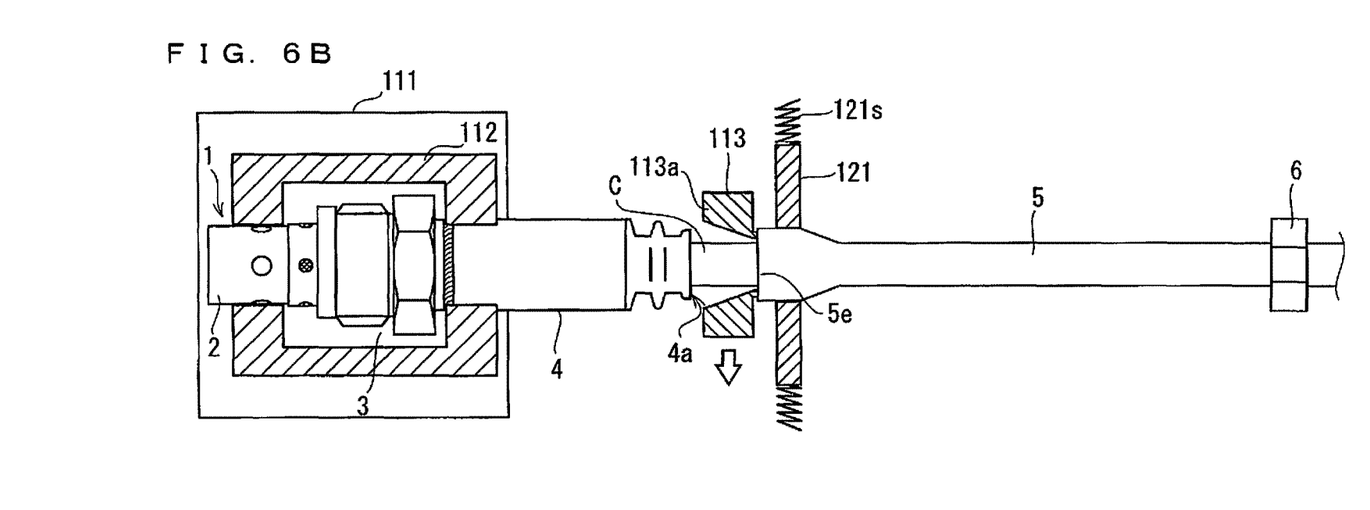

When this engagement has been completed, the tube-end holding-jig driving mechanism 120 is activated, so that, as indicated by arrows AR7 in FIG. 6A, respective one end portions of the pair of the tube-end holding jigs 121 are gotten closer to the corresponding arm portions 113b in the pair of the tube-end opening jigs 113 which are covered with the protection tube 5 and, further, are brought into contact with the protection tube 5 as illustrated in FIG. 6B.

This is realized by an effect of energizing springs 121s which are provided on the respective other end portions of the pair of the tube-end holding jigs 121, as illustrated in FIG. 6B. However, in FIGS. 3 to 6A, these energizing springs 121s are omitted.

More specifically, until the time point when the protection tube 5 has been engaged with the pair of the tube-end opening jigs 113, the pair of the tube-end holding jigs 121 are held by the tube-end holding-jig driving mechanism 120 in such a way as to maintain the energizing springs 121s at a compressed state. At the time point when this engagement has been attained, the pair of the tube-end holding jigs 121 are released to cancel the compressed state of the energizing springs 121s. Then, the energizing springs 121s stretch due to their restoration forces, but by providing the energizing springs 121s such that they remain in a state of being shrunk from a natural length even in the state where the pair of the tube-end holding jigs 121 are in contact with the protection tube 5, the pair of the tube-end holding jigs 121 being in contact with the protection tube 5 are caused to energize the protection tube 5 due to the restoration forces of the energizing springs 121s. Namely, due to the restoration forces of the energizing springs 121s included in the pair of the tube-end holding jigs 121, it is possible to realize a state where the protection tube 5 is held through pinching by the pair of the tube-end holding jigs 121 and the arm portions 113b in the pair of the tube-end opening jigs 113.

The arm portions 113b and the tapered portions 113c, at least, in the pair of the tube-end opening jigs 113, and at least the portions of the pair of the tube-end holding jigs 121 which come into contact with the protection tube 5 are formed from materials (such as plastics, for example) which do not injure the protection tube 5.

Figure 7A:
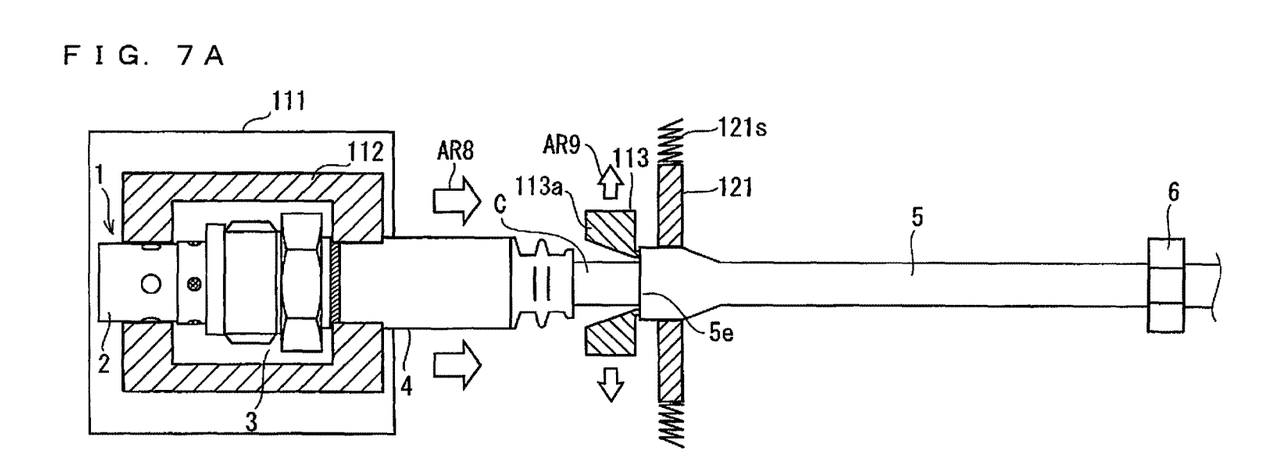
Figure 7B:
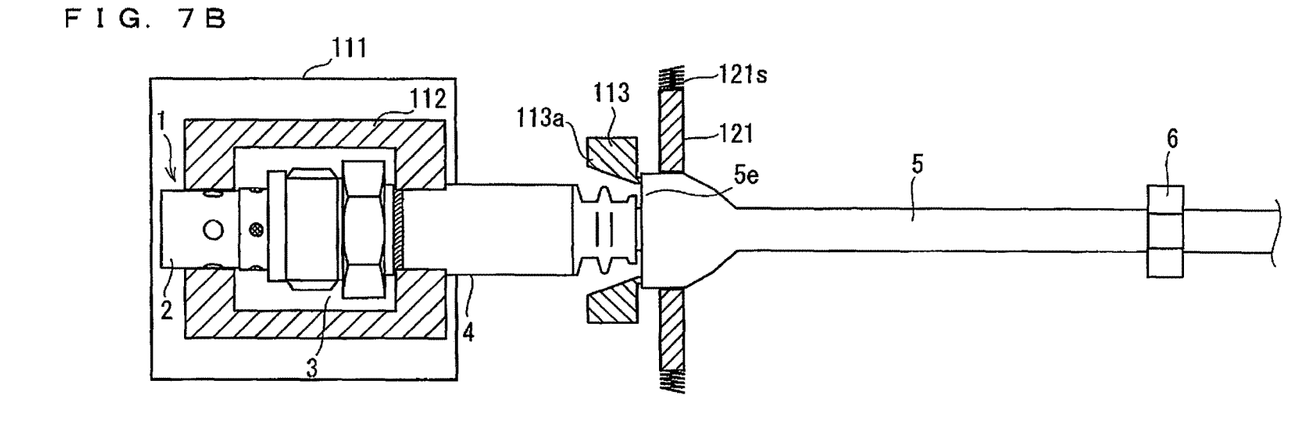

When this holding of the protection tube 5 have been realized, subsequently, the main-body fixing and transfer mechanism 110 moves the main-body placement portion 111 to get the gas sensor 1 closer to the protection tube 5, as indicated by arrows AR8 in FIG. 7A. At this time, along with this movement of the main-body placement portion 111, the pair of the tube-end opening jigs 113 are moved in the direction in which they are spaced apart from each other, as indicated by arrows AR9. Further, at this time, the pair of the tube-end holding jigs 121 follow the pair of the tube-end opening jigs 113 being spaced apart from each other, due to the shrink of the energizing springs. This further expands the one end portion 5e of the protection tube 5 which is held through pinching by the pair of the tube-end opening jigs 113 and the pair of the tube-end holding jigs 121, as illustrated in FIG. 7B. Namely, getting the gas sensor 1 closer to the protection tube 5 by moving the main-body placement portion 111, and the expanding of the one end portion 5e of the protection tube 5 are performed in conjunction with each other.

Figure 8A:
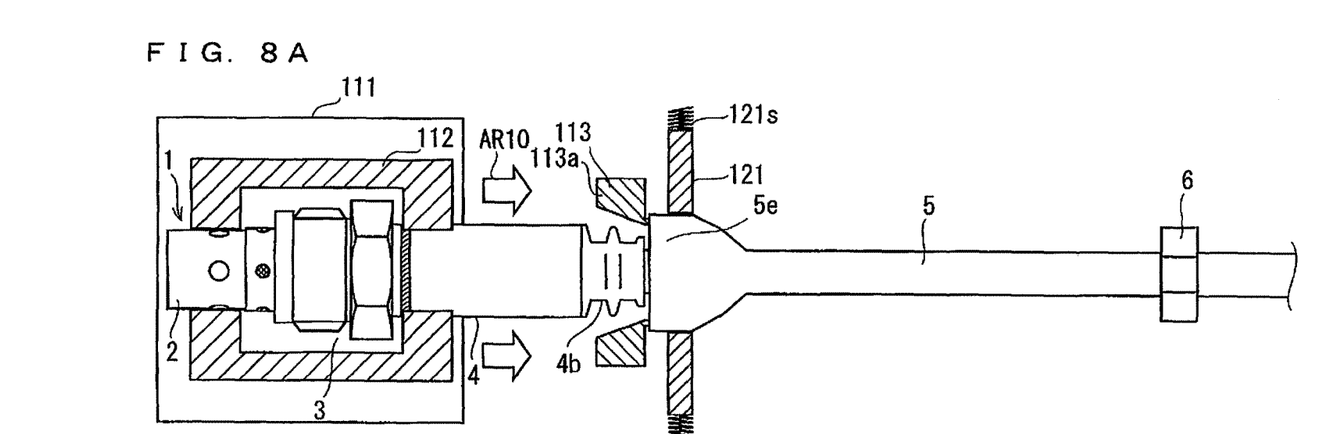

As indicated by arrows AR10 in FIG. 8A, the main-body placement portion 111 is further moved to further get the gas sensor 1 closer to the protection tube 5, and, finally, the end portion 4b of the second cover 4 in the gas sensor 1 is inserted into the expanded one end portion 5e of the protection tube 5, so that this end portion 4b comes into contact with the inner surface of the protection tube 5. Even after this contacting, the main-body placement portion 111 is moved, and the protection tube 5 having been engaged with the pair of the tube-end opening jigs 113 is moved together with the gas sensor 1 in such a way as to be pressed by the end portion 4b of the second cover 4 and, along therewith, the protection tube 5 is gradually released from the engagement with the pair of the tube-end opening jigs 113.

Figure 8B:
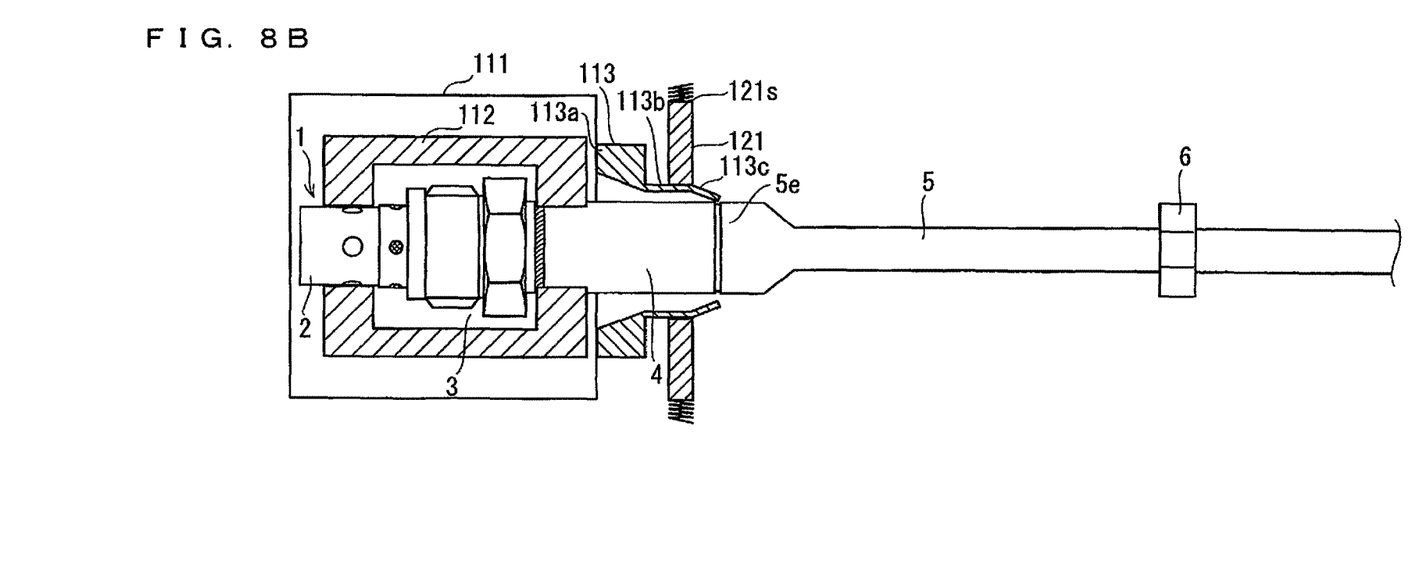

Then, the expanded one end portion 5e of the protection tube 5 is sequentially shrunk from its portion which has been released from the engagement and is brought into intimate contact with the end portion 4b of the second cover 4 which exists inside it. When the protection tube 5 has been completely released from the engagement with the pair of the tube-end opening jigs 113, there is realized a state where the end portion of the protection tube 5 is mounted to the end portion 4b of the second cover 4, as illustrated in FIG. 8B.

As described above, with the fitting processing according to the present preferred embodiment, the second cover 4 in the gas sensor 1 is intruded into the protection tube 5 being held through pinching, while the one end portion 5e is maintained at an opened state. Therefore, it is possible to fit the protection tube 5 to the gas sensor 1 without inducing displacements of the protection tube 5.

Further, the fitting apparatus 100 is configured to perform movement of the main-body placement portion 111 on and to which the gas sensor 1 is placed and fixed in the fitting processing and operations with the pair of the tube-end opening jigs 113, in conjunction with each other. This can improve the certainty of fitting of the protection tube 5 to the gas sensor 1. This contributes to improvement of the yield of the fitting processing.

Also, at the time when the end portion 4b of the second cover 4 of the gas sensor 1 has come into contact with the inner surface of the protection tube 5, the tube-end holding-jig driving mechanism 120 may slightly withdraw the pair of the tube-end holding jigs 121, thereby bringing the protection tube 5 and the pair of the tube-end holding jigs 121 into a state of not being in contact with each other.

Figure 9:
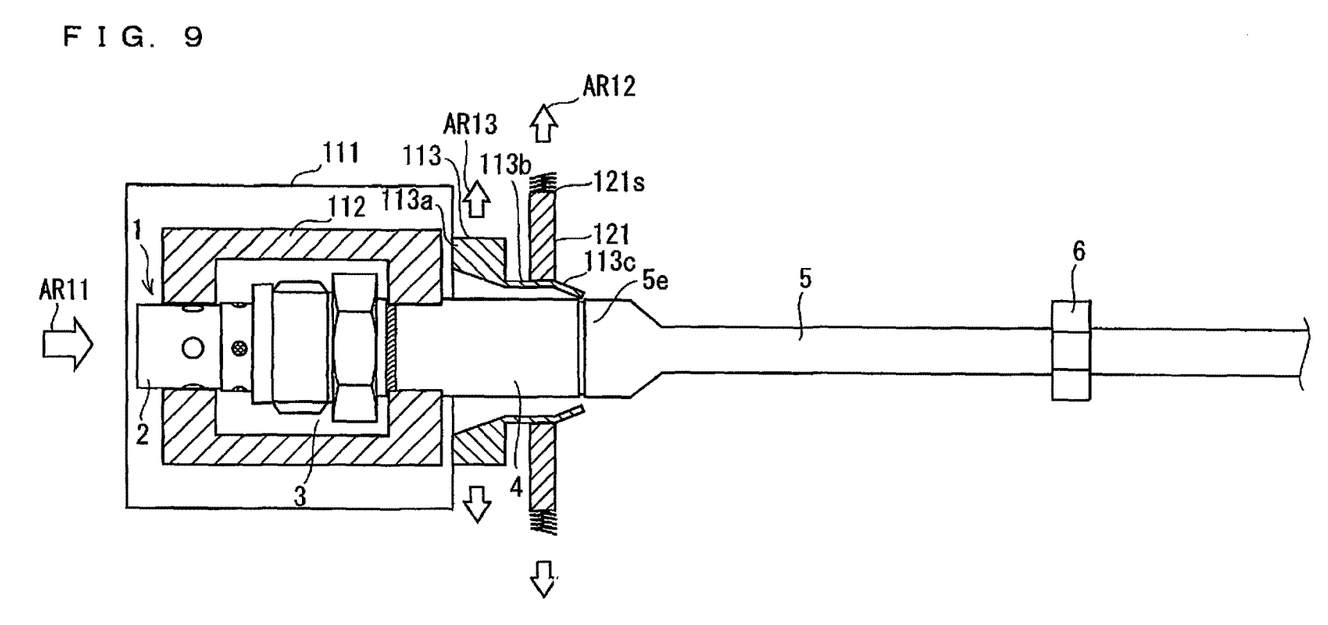

After the mounting of the protection tube 5 to the end portion 4b of the second cover 4 has been realized, subsequently, the main-body placement portion 111 is further moved as indicated by an arrow AR11 in FIG. 9 and, further, the main-body fixing and transfer mechanism 110 and the tube-end holding-jig driving mechanism 120 are activated, so that the pair of the tube-end opening jigs 113 and the pair of the tube-end holding jigs 121 are withdrawn from the side of the gas sensor 1, as indicated by arrows AR12 and AR13.

Figure 10:
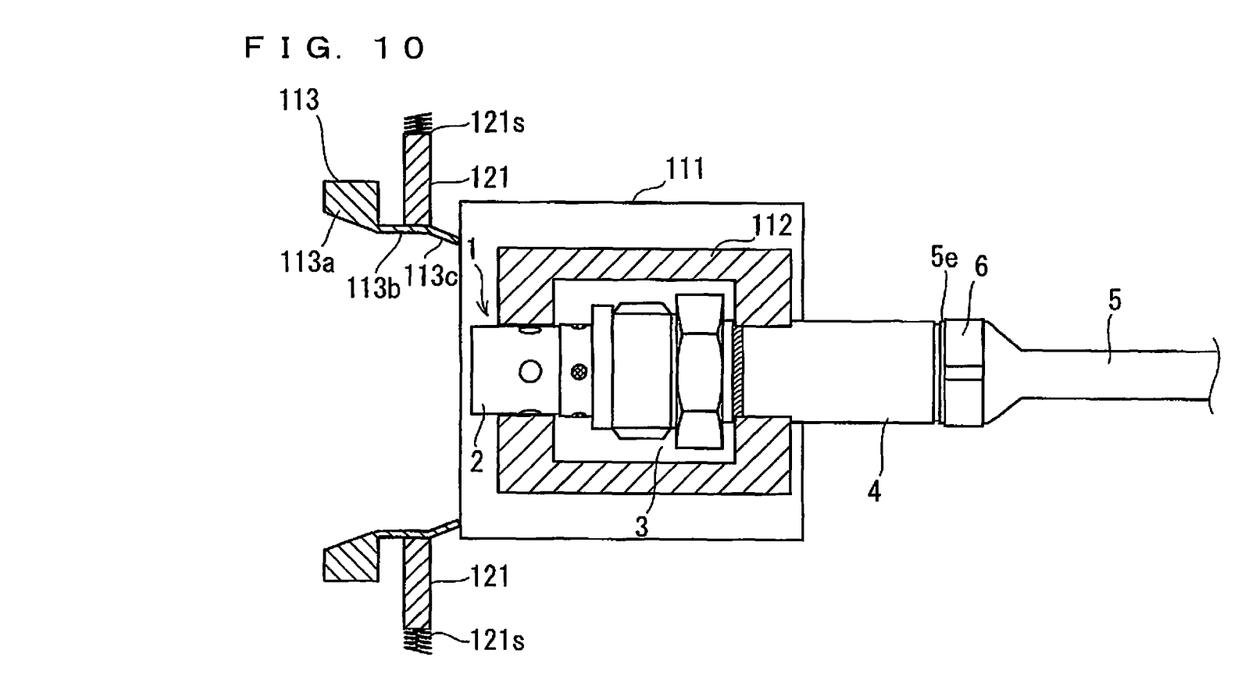

The movement of the main-body placement portion 111 is performed, until the fitted portion of the protection tube 5 reaches the position where the clamp securing mechanism 140 holds the ear clamp 6. When this fitted portion has reached the position where the ear clamp 6 is held, the clamp securing mechanism 140 fastens the ear clamp 6. Thus, the gas sensor 1 and the protection tube 5 are secured to each other through the ear clamp 6 having been reduced in diameter. FIG. 10 illustrates a state where this securing has been performed.

By providing the position where the clamp securing mechanism 140 holds the ear clamp 6, near the position where the fitting of the protection tube 5 to the end portion 4b of the second cover 4 is to be completed, it is possible to immediately fasten the ear clamp 6 after the fitting of the protection tube, which enables securing the protection tube 5 thereto more certainly, without inducing displacements of the fitted protection tube 5 due to some reasons.

After the protection tube 5 has been secured to the gas sensor 1 in the aforementioned way, the main-body fixing and transfer mechanism 110 cancels the fixing of the gas sensor 1 by the main-body fixing jigs 112. Thus, the series of fitting processing has been completed.

As described above, according to the present preferred embodiment, the processing for fitting the protection tube for protecting the cables to the gas sensor is performed as follows. That is, the pair of the tube-end opening jigs are inserted into the inside of the protection tube through one end portion of the protection tube, and this end portion of the protection tube is engaged with the pair of the tube-end opening jigs for maintaining this end portion at an opened state and, thereafter, the protection tube is held through pinching between the pair of the tube-end holding jigs and the pair of the tube-end opening jigs which are placed outside the protection tube. This enables fitting the protection tube to the gas sensor without inducing displacements of the protection tube.

Furthermore, the pair of the tube-end opening jigs are provided with the tapered portions such that the interval between the pair of the respective companion tapered portions decreases with decreasing distance to their tip ends, and these tapered portions are inserted into the inside of the protection tube. This enables easily and certainly engaging the protection tube with the pair of the tube-end opening jigs, without inducing cracks and breakages at its end portion.

In addition, in the fitting processing, movement of the placement portion on and to which the gas sensor is placed and fixed and operations with the pair of the tube-end opening jigs can be performed in conjunction with each other and, further, the clamp mechanism for fastening the fitted portion of the protection tube with the ear clamp can be placed near the position where the fitting is to be completed, which can improve the certainty of fitting and securing of the protection tube to the gas sensor, thereby increasing the yield of the gas sensor.

While the invention has been shown and described in detail, the foregoing description is in all aspects illustrative and not restrictive. It is therefore understood that numerous modifications and variations can be devised without departing from the scope of the invention.

What is claimed is:

1. A method for fitting a protection tube for protecting cables to a gas sensor, comprising the steps of:
   a) maintaining one end portion of said protection tube at an opened state with a tube-end opening jig, said tube-end opening jig being configured to be inserted into inside of said protection tube through said one end portion of said protection tube to engage said one end portion of said protection tube with said tube-end opening jig;
   b) holding said protection tube through pinching between a tube-end holding jig and said tube-end opening jig, said tube-end holding jig being configured to come into contact with said protection tube at said one end portion which is engaged with said tube-end opening jig, from outside of said protection tube; and
   c) inserting said gas sensor into inside of said protection tube being held through pinching by said tube-end holding jig and said tube-end opening jig, the insertion of said gas sensor into the inside of said protection tube being configured to be continued even after an end portion of said gas sensor comes into contact with an inner surface of said protection tube, while the engagement of said protection tube with said tube-end opening jig is gradually released, thereby fitting said protection tube to said gas sensor.

2. The method for fitting a protection tube to a gas sensor, according to claim 1, wherein
   said tube-end opening jig comprises a pair of tube-end opening jigs, and
   each of said pair of the tube-end opening jigs has a tapered portion such that a distance therebetween gradually decreases toward a tip end of said tapered portion in each of said pair of the tube-end opening jigs, and
   in said step a), said tapered portions are inserted into the inside of said protection tube.

3. The method for fitting a protection tube to a gas sensor, according to claim 2, wherein
   said tube-end holding jig includes an energizing member, and
   in said step b), said protection tube is held through the pinching between said tube-end holding jig and said tube-end opening jig by an energizing force of said energizing member.

4. The method for fitting a protection tube to a gas sensor, according to claim 2, further comprising the step of
   d) securing said protection tube to said gas sensor by fastening said gas sensor at a portion to which said protection tube has been fitted, with an annular-shaped fastening member, from outside of said protection tube.

5. The method for fitting a protection tube to a gas sensor, according to claim 1, wherein
   said tube-end holding jig includes an energizing member, and
   in said step b), said protection tube is held through the pinching between said tube-end holding jig and said tube-end opening jig by an energizing force of said energizing member.

6. The method for fitting a protection tube to a gas sensor, according to claim 5, further comprising the step of
   d) securing said protection tube to said gas sensor by fastening said gas sensor at a portion to which said protection tube has been fitted, with an annular-shaped fastening member, from outside of said protection tube.

7. The method for fitting a protection tube to a gas sensor, according to claim 1, further comprising the step of
   d) securing said protection tube to said gas sensor by fastening said gas sensor at a portion to which said protection tube has been fitted, with an annular-shaped fastening member, from outside of said protection tube.

\* \* \* \* \*